US009867553B2

(12) United States Patent
Garaycochea

(10) Patent No.: US 9,867,553 B2
(45) Date of Patent: Jan. 16, 2018

(54) ATTACHABLE NASAL CANNULA

(71) Applicant: Christian I. Garaycochea, Las Vegas, NV (US)

(72) Inventor: Christian I. Garaycochea, Las Vegas, NV (US)

(*) Notice: Subject to any disclaimer, the term of this patent is extended or adjusted under 35 U.S.C. 154(b) by 714 days.

(21) Appl. No.: 14/334,535

(22) Filed: Jul. 17, 2014

(65) Prior Publication Data

US 2016/0015296 A1    Jan. 21, 2016

(51) Int. Cl.

| *A61B 5/097* | (2006.01) |
|---|---|
| *A61M 16/06* | (2006.01) |
| *A61M 16/08* | (2006.01) |
| *A61M 16/10* | (2006.01) |
| A61B 5/083 | (2006.01) |
| A61B 5/00 | (2006.01) |
| A61B 5/145 | (2006.01) |

(52) U.S. Cl.
CPC ......... *A61B 5/097* (2013.01); *A61M 16/0672* (2014.02); *A61M 16/0688* (2014.02); *A61M 16/085* (2014.02); *A61M 16/1005* (2014.02); A61B 5/0836 (2013.01); A61B 5/14542 (2013.01); A61B 5/6819 (2013.01); A61B 5/6833 (2013.01); A61M 2016/103 (2013.01); A61M 2202/0208 (2013.01); A61M 2205/3327 (2013.01); A61M 2230/432 (2013.01)

(58) Field of Classification Search
CPC .......... A61M 16/0688; A61M 16/1055; A61M 16/085; A61M 16/0672; A61M 2016/103; A61M 16/1005; A61M 2230/432; A61M 2202/0208; A61B 5/6833; A61B 5/6819; A61B 5/0836; A61B 5/097; A61B 5/14542; Y10S 128/26; A61F 13/02; A61F 13/0246; A61F 13/0025

USPC .......... 128/204.22, 207.17, DIG. 26; 24/304, 24/369, DIG. 11; 604/174, 180; 602/41, 602/52, 45, 58, 78, 79; 206/440, 63.3

See application file for complete search history.

(56) References Cited

U.S. PATENT DOCUMENTS

| 5,046,491 | A * | 9/1991 | Derrick | A61B 5/097 |
| | | | | 128/200.24 |
| 5,676,137 | A * | 10/1997 | Byrd | A61G 7/0503 |
| | | | | 128/207.14 |
| 5,682,881 | A * | 11/1997 | Winthrop | A61M 16/0666 |
| | | | | 128/200.26 |
| 7,024,235 | B2 * | 4/2006 | Melker | A61B 5/0873 |
| | | | | 600/340 |
| 2010/0069770 | A1 * | 3/2010 | Girshin | A61B 5/0833 |
| | | | | 600/532 |
| 2012/0226182 | A1 * | 9/2012 | Bonato | A61B 5/082 |
| | | | | 600/537 |

* cited by examiner

*Primary Examiner* — (Jackie) Tan-Uyen T Ho
*Assistant Examiner* — Margaret Luarca
(74) *Attorney, Agent, or Firm* — Holland & Hart LLP

(57) ABSTRACT

A respiratory gas measurement system is described. In one embodiment, the respiratory gas measurement system includes a chamber and an adhesive pad. The chamber is configured to collect a respiratory gas. The adhesive pad includes a substrate. At least a portion of a first surface of the substrate is covered with adhesive. The adhesive on the first surface of the substrate attaches the adhesive pad to a first surface of the chamber. The adhesive pad enables the chamber to attach to a surface of another nasal cannula.

19 Claims, 12 Drawing Sheets

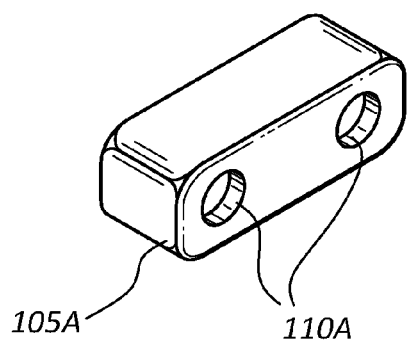
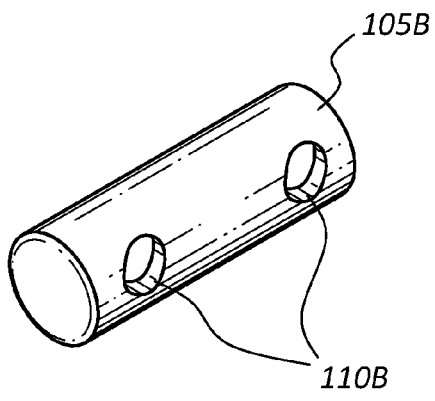
FIG. 1A  FIG. 1B
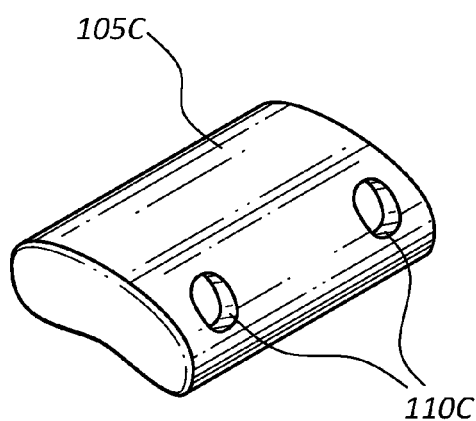
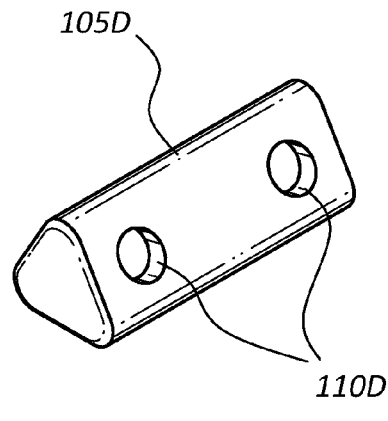
FIG. 1C  FIG. 1D

ATTACHABLE NASAL CANNULA

TECHNICAL FIELD

The present disclosure relates generally to a nasal cannula and methods, and more particularly, to systems and methods for attaching an attachable nasal cannula to a conventional nasal cannula.

BACKGROUND

A nasal cannula is a medical device that may be used to deliver supplemental oxygen to a person in certain medical situations. The nasal cannula may include a tube that at one end splits into two prongs, the two prongs being placed in the nostrils. The other end of the tube may be connected to an oxygen supply. In some cases, a nasal cannula may be used to measure respiratory gases. Capnography is the monitoring of the concentration or partial pressure of carbon dioxide ($CO_2$) in the respiratory gases. Capnography may be used as a monitoring tool during anesthesia and intensive care.

Capnography may be presented as a capnogram, a graph of expiratory $CO_2$ plotted against time. A typical capnogram for patients is characterized by a set of specific elements. Typically, a capnogram is divided into 4 distinct phases. In phase I, the $CO_2$ concentration starts at zero, used as a respiratory baseline, typically 0 millimeters of mercury (mmHg). Phase II indicates the sharp expiratory upstroke of expired $CO_2$ as alveolar gas exits the airway. The sharp rise in expired $CO_2$ levels out in phase III, resulting in a maximum $CO_2$ concentration being reached. This maximum $CO_2$ concentration is referred to as end-tidal $CO_2$ ($ETCO_2$). With the start of inhalation during phase IV, the $CO_2$ concentration decreases to zero (i.e., 0 mmHg) as atmospheric air again enters the airway. The amplitude of the capnogram depends on the $ETCO_2$ concentration and the width depends on the expiratory time. A characteristic shape exists for all subjects with normal lung function. Accordingly, advancements in capnography enables an anesthesiologist to monitor a patient's vital signs more reliably. Nevertheless, benefits may be realized by providing systems and methods for improving capnography systems.

SUMMARY

According to at least one embodiment, a respiratory gas measurement system is described. In one embodiment, the respiratory gas measurement system may include a chamber and an adhesive pad. The chamber may be configured to collect a respiratory gas. The adhesive pad may include a substrate. At least a portion of a first surface of the substrate may be covered with adhesive. The adhesive on the first surface of the substrate attaches the adhesive pad to a first surface of the chamber. The adhesive pad may enable the chamber to attach to a surface of a nasal cannula.

In some embodiments, at least a portion of a second surface of the substrate is covered with adhesive. In some cases, the adhesive on the second surface of the substrate attaches the adhesive pad to a surface of a nasal cannula. The adhesive pad may include a flexible adhesive strip. The flexible adhesive strip may include a substrate strip. The substrate strip may be an extension of the substrate of the adhesive pad. In some cases, at least a portion of the substrate strip may be covered with adhesive. In one embodiment, at least a second surface of the chamber may include an opening. The opening may be configured as an inlet and/or outlet for the respiratory gas.

In one embodiment, a tubular stem may extend from a third surface of the chamber. The tubular stem may be configured as an outlet and/or inlet for the respiratory gas. In some cases, the tubular stem may include a flexible adhesive stem strip. The flexible adhesive stem strip may be configured to adhesively join the tubular stem to a tube of a nasal cannula. The tubular stem may include a connector. The connector may be configured to enable measurement of the respiratory gas. In some cases, the tubular stem may include a semi-circular clip, the semi-circular clip being configured to mechanically join the tubular stem to a tube of a nasal cannula.

An attachable nasal cannula is also described. The attachable nasal cannula may include a chamber and an adhesive pad. The chamber may be configured to collect a respiratory gas. The adhesive pad may include a substrate. At least a portion of a first surface of the substrate may be covered with adhesive. The adhesive on the first surface of the substrate attaches the adhesive pad to a first surface of the chamber. The adhesive pad may enable the chamber to attach to a surface of another nasal cannula.

A method for an attachable nasal cannula is described. In one embodiment, the method may include attaching a flexible adhesive strip to a chamber configured to collect a respiratory gas. The flexible adhesive strip may include a substrate. At least a portion of the substrate may be covered with adhesive. The method may include attaching, via the flexible adhesive strip, the chamber to a nasal cannula. The method may include looping the flexible adhesive strip around the chamber and the nasal cannula to attach the chamber to the nasal cannula.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIGS. 1A-1D illustrate perspective views of several embodiments of chambers with which the present systems and methods may be implemented;

Figure 2A:
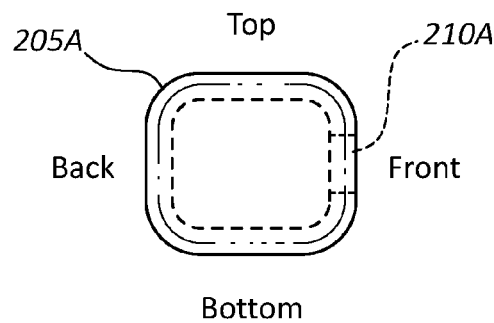
FIGS. 2A-2D illustrate side-views of several embodiments of chambers in relation to the chambers of FIGS. 1A-1D.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

As described above, capnography is the monitoring of the concentration or partial pressure of carbon dioxide ($CO_2$) in the respiratory gases. Its main development has been as a monitoring tool for use during anesthesia and intensive care. It is usually presented as a graph of expiratory $CO_2$ plotted against time, or, less commonly, but more usefully, expired volume. The plot may also show the inspired $CO_2$, which is of interest when rebreathing systems are being used. The systems and methods disclosed herein are generally related to aspects of measuring end-tidal $CO_2$ ($ETCO_2$). Monitoring $ETCO_2$ may include measuring expired respiratory gases using a nasal cannula. While not meant to be limiting, the systems and methods disclosed herein are used to affix a first nasal cannula to a second nasal cannula to measure $ETCO_2$. It will be appreciated that the systems and methods disclosed herein may be applicable to other respiratory monitoring applications.

Typically, a patient's oxygen level or oxygen saturation in the blood may be measured using pulse oximetry. The medical field uses pulse oximetry as a noninvasive, painless, general indicator of oxygen delivery to the peripheral tissues of the patient. Transmissive pulse oximetry may include placing a sensor on a thin part of the patient's body, such as a fingertip or earlobe, or in the case of an infant, across a foot. Light of two wavelengths is passed through the patient to a photodetector. The changing absorbance at each of the wavelengths is measured, allowing determination of the absorbances due to the pulsing arterial blood alone, excluding venous blood, skin, bone, muscle, fat, etc. In some cases, reflectance pulse oximetry may be used as an alternative to transmissive pulse oximetry. Pulse oximetry, however, has several drawbacks. Vasodilation and pooling of venous blood in the head due to compromised venous return to the heart, as occurs with congenital heart disease patients, can cause a combination of arterial and venous pulsations in the forehead region and lead to spurious SpO2 (Saturation of peripheral oxygen) results. Accordingly, during procedures done under sedation, capnography provides more useful information such as on the frequency and regularity of ventilation, than pulse oximetry alone.

Capnography directly reflects the continuous elimination of $CO_2$ by a patient's lungs. Indirectly, it reflects the production of $CO_2$ by tissues and the circulatory transport of $CO_2$ to the lungs. Capnography has been shown to be an effective method for early detection of adverse respiratory events such as hypoventilation, esophageal intubation and circuit disconnection. Capnography and pulse oximetry together could have helped in the prevention of 93% of avoidable anesthesia mishaps according to an American Society of Anesthesiologists (ASA) closed claim study. Thus, using capnography in conjunction with pulse oximetry may increases an anesthesiologist's ability to prevent injury to the patient.

As stated above, the capnogram is a direct monitor of the inhaled and exhaled concentration or partial pressure of $CO_2$, and an indirect monitor of the $CO_2$ partial pressure in the arterial blood. In healthy individuals, the difference between arterial blood and expired gas $CO_2$ partial pressures is very small. In the presence of most forms of lung disease, and some forms of congenital heart disease (the cyanotic lesions) the difference between arterial blood and expired gas increases and can exceed 1 kilopascals (kPa). Capnography provides a rapid and reliable method to detect life-threatening conditions (malposition of tracheal tubes, unsuspected ventilatory failure, circulatory failure and defective breathing circuits) and to circumvent potentially irreversible patient injury.

Because it provides a breath by breath measurement of a patient's ventilation, capnography quickly reveals a worsening trend in a patient's condition by providing surgeons, anesthesiologists, and paramedics alike with an early warning system into a patient's respiratory status. Clinical studies indicate the criticality of capnography in a growing number of medical situations including those involving asthma, congestive heart failure, diabetes, circulatory shock, pulmonary embolus, acidosis, and other conditions, with several potential implications for the pre-hospital use as well.

Based on the systems and methods described herein, surgeons, paramedics, anesthesiologists, and the like are enabled to monitor the $ETCO_2$ status of non-intubated patients easily and effectively by using an attachable nasal cannula that collects carbon dioxide expired by the patient. In the case of paramedics and other pre-hospital and/or pre-surgery environments, high $ETCO_2$ reading in a patient with altered mental status or severe difficulty breathing may indicate hypoventilation and a possible need for the patient to be intubated. Additionally, low $ETCO_2$ readings from patients may indicate a hyperventilation situation.

Traditionally, a hospital may use a single conventional nasal cannula to deliver supplemental oxygen or airflow to a patient under general anesthesia. For most anesthesia professionals, oxygen administration by nasal cannula or mask (open oxygen delivery) is routine when providing sedation, and is a fundamental strategy for preventing hypoxemia. In order to monitor $ETCO_2$, the conventional nasal cannula may be replaced with one customized to deliver oxygen as well as measure $CO_2$. These dual-purpose nasal cannulas, however, present a number of problems to medical caregivers. Dual-purpose nasal cannulas may be significantly more expensive than conventional nasal cannulas, in some cases on the order of four to five times more expensive than conventional nasal cannulas. Based on the narrow margins under which many hospitals operate, monitoring of $ETCO_2$ on top of oxygen delivery imposes a significant expense. Accordingly, providing a cost-effective and simple to use alternative to the dual-purpose nasal cannulas enables more hospitals and paramedics to monitor ETCO2 economically. Moreover, lowering the costs of ETCO2 monitoring not only enables more hospitals and paramedics to monitor ETCO2, but enables the same hospitals and paramedics to expand the use of ETCO2 monitoring into further applications. Providing hospitals and paramedics with a cost effective and simple to use attachable nasal cannula enables the hospitals and paramedics to economically convert the low-cost conventional nasal cannulas into nasal cannulas that can monitor ETCO2. Additionally, many dual-purpose nasal cannulas provide ineffective measurements of expired CO2.

In one conventional dual-purpose design, the function of the two prongs may be divided, one prong being configured for delivery of oxygen, the other prong being configured for measuring CO2. The chamber may be divided into two separate, sealed-off chambers, each side of the chamber including its own stem. The first stem connects to an oxygen source to provide oxygen to the first chamber, which is inhaled by the patient through the first prong. The second prong captures CO2 exhaled by the patient, which is collected in the second chamber, the second stem delivering the collected CO2 to a measuring device. Most people, however, do not expire and/or inspire equally from each nostril. Most people have to some degree a deviated septum, resulting in one nostril being able to breathe more freely than the other. Thus, such an ineffective design may deliver oxygen wastefully to an obstructed nostril and/or inaccurately monitor CO2 expired from an obstructed nostril. Accordingly, several benefits may be realized by providing a cost effective and simple to use attachable nasal cannula to enable hospitals and paramedics to economically convert a low-cost conventional nasal cannula into a nasal cannula capable of delivering oxygen while monitoring ETCO2.

In a first exemplary embodiment, described with reference to FIGS. 1-11, various aspects of an attachable nasal cannula are depicted. An attachable nasal cannula may include a chamber of various shapes and/or sizes. For example, the shape of the chamber may include a cylindrical chamber, a hexagonal prism, a triangular prism, a rectangular prism or cuboid, and the like. The chamber may include one or more ports or holes through which respiratory gases may be captured and collected in the chamber. The chamber may include one or more stems through which the gases collected in the chamber may be measured to create a capnogram. One or more adhesive strips may be coupled to the chamber and/or the one or more stems, enabling the attachable nasal cannula to be attached to another device. In one example, the attachable nasal cannula may be attached to another nasal cannula via one or more adhesive strips. For instance, the attachable nasal cannula may be attached to the cost-effective conventional nasal cannula. Thus, a medical caregiver may deliver oxygen to the patient continuing to use the conventional nasal cannulas while easily affixing the attachable nasal cannula to the conventional nasal cannula in order to monitor expired CO2 as well.

Referring now to FIGS. 1 and 2, a chamber depicted in various shapes. Any one of the depicted chambers may be used as the chamber of an attachable nasal cannula. Although the chambers of FIG. 1 are depicted with two holes or breathing ports, it is understood that any one of the chambers may include a single hole or breathing port. In some cases, a chamber may include more than two holes or breathing ports. In one embodiment, a hole may be a single round hole. In some cases, the single port may be in an oval shape. For example, in some cases, the longest part of the oval runs from side to side along the length of the front of the chamber, on the same surface upon which the holes are depicted in FIG. 1.

Referring now to FIGS. 1A-1D, FIG. 1A depicts a chamber 105A. In some embodiments, FIG. 1A depicts one example of a chamber for collecting respiratory gases. The chamber 105A may be made from any combination of plastics, poly vinyl chloride (PVC), latex, silicone, natural polymers, synthetic polymers, and the like. As depicted, chamber 105A includes two breathing ports 110A. As depicted, chamber 105A is configured in the shape of a rectangular prism or cuboid. Chamber 105A may be configured to collect expired respiratory gases and/or deliver respiratory gases. In one embodiment, chamber 105A may be an element of an attachable nasal cannula. Accordingly, breathing ports 110A may be configured to capture respiratory gases and collect them into chamber 105A. In some embodiments, chamber 105A may collect expired CO2. Thus, in some cases, chamber 105A may be used to monitor ETCO2 in conjunction with a nasal cannula configured to deliver oxygen to a patient.

In one embodiment, FIG. 1B depicts another example embodiment of a chamber for collecting respiratory gases. FIG. 1B depicts a chamber 105B. The chamber 105B may be made from any combination of plastics, PVC, latex, silicone, natural polymers, synthetic polymers, and the like. As depicted, chamber 105B includes two breathing ports 110B. As depicted, chamber 105B is configured in the shape of a cylinder or cylindrical prism. Chamber 105B may be configured to collect expired respiratory gases and/or deliver respiratory gases. In one embodiment, chamber 105B may be an element of an attachable nasal cannula. Accordingly, breathing ports 110B may be configured to capture respiratory gases and collect them into chamber 105B. In some embodiments, chamber 105B may collect expired CO2. Thus, in some cases, chamber 105B may be used to monitor ETCO2 in conjunction with a nasal cannula configured to deliver oxygen to a patient.

In one embodiment, FIG. 1C depicts another example embodiment of a chamber for collecting respiratory gases. FIG. 1C depicts a chamber 105C. The chamber 105C may be made from any combination of plastics, PVC, latex, silicone, natural polymers, synthetic polymers, and the like. As depicted, chamber 105C includes two breathing ports 110C. As depicted, chamber 105C is configured in a kidney shape or reniform prism. Chamber 105C may be configured to collect expired respiratory gases and/or deliver respiratory gases. In one embodiment, chamber 105C may be an element of an attachable nasal cannula. Accordingly, breathing ports 110C may be configured to capture respiratory gases and collect them into chamber 105C. In some embodiments, chamber 105C may collect expired CO2. Thus, in some cases, chamber 105C may be used to monitor ETCO2 in conjunction with a nasal cannula configured to deliver oxygen to a patient.

In one embodiment, FIG. 1D depicts another example embodiment of a chamber for collecting respiratory gases. FIG. 1D depicts a chamber 105D. The chamber 105D may be made from any combination of plastics, PVC, latex, silicone, natural polymers, synthetic polymers, and the like. As depicted, chamber 105D includes two breathing ports 110D. As depicted, chamber 105D is configured in the shape of deltoid or triangular prism. Chamber 105D may be configured to collect expired respiratory gases and/or deliver respiratory gases. In one embodiment, chamber 105D may be an element of an attachable nasal cannula. Accordingly, breathing ports 110D may be configured to capture respiratory gases and collect them into chamber 105D. In some embodiments, chamber 105D may collect expired CO2. Thus, in some cases, chamber 105D may be used to monitor ETCO2 in conjunction with a nasal cannula configured to deliver oxygen to a patient.

Referring now to FIGS. 2A-2D, FIG. 2A depicts a cross-sectional view of a chamber 205A. In some embodiments, FIG. 2A depicts one example of a chamber for collecting respiratory gases. In one embodiment, chamber 205A may depict an example of a cross-section of chamber 105A depicted in FIG. 1A. As depicted, chamber 205A includes at least one breathing port 210A. As depicted, chamber 205A is configured in the shape of a rectangular prism or cuboid. As with the breathing ports 110A of FIG. 1A, the at least one breathing port 210A may be configured to capture respiratory gases and collect them into chamber 205A. The at least one breathing port 210A may be located on one surface of chamber 205A. As illustrated, the surface of chamber 205A upon which the at least one breathing port 210A may be located may be referred to as a front surface. The surface of chamber 205A opposite that of the surface containing the at least one breathing port 210A, as illustrated, may be referred to a back surface. As illustrated, a first surface adjacent to the surface containing the at least one breathing port 210A may be referred to as a bottom surface, and a second surface adjacent to the surface containing the at least one breathing port 210A may be referred to as a top surface. Thus, relative to the chamber 205A resting on a flat surface such as a desktop or medical tray, the surface of chamber 205A resting on the flat surface of the desktop or tray may be referred to as the bottom surface of chamber 205A and the surface of the chamber 205A opposite and parallel to the bottom surface may be referred to as the top surface. In some embodiments, chamber 205A may collect expired CO2. Thus, in some cases, chamber 205A may be used to monitor ETCO2 in conjunction with a nasal cannula configured to deliver oxygen to a patient.

Figure 2B:
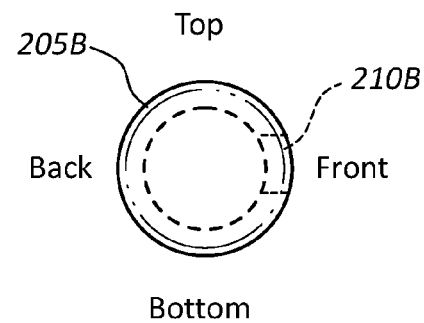

As illustrated, FIG. 2B depicts a cross-sectional view of a chamber 205B. In some embodiments, FIG. 2B depicts one example of a chamber for collecting respiratory gases. In one embodiment, chamber 205A may depict an example of a cross-section of chamber 105B depicted in FIG. 1B. As shown in FIG. 2B, chamber 205B includes at least one breathing port 210B. As depicted, chamber 205B is configured in the shape of a rectangular prism or cuboid. As with the breathing ports 110B of FIG. 1B, the at least one breathing port 210B may be configured to capture respiratory gases and collect them into chamber 205B. The at least one breathing port 210B may be located on a portion of the surface of the cylindrical chamber 205B. As illustrated, the portion of the surface of chamber 205B upon which the at least one breathing port 210B may be located may be referred to as a front surface. The portion of the surface of chamber 205B opposite that of the portion of the surface containing the at least one breathing port 210B, as illustrated, may be referred to a back surface. If the cross-sectional view of chamber 205B were divided into 360 degrees, with the portion of surface of chamber 205B containing the at least one breathing port 210B at 0 degrees, then the back surface would be situated at 180 degrees. Furthermore, a portion of the surface of chamber 205B at 90 degrees may be referred to as a top surface of chamber 205B, and a portion of the surface of chamber 205B at 270 degrees may be referred to as a bottom surface of chamber 205B. Thus, relative to the chamber 205B resting on a flat surface such as a desktop or medical tray, the surface of chamber 205B resting on the flat surface of the desktop or table may be referred to as the bottom surface of chamber 205B and the surface of the chamber 205B opposite the bottom surface may be referred to as the top surface. In some embodiments, chamber 205B may collect expired CO2. Thus, in some cases, chamber 205B may be used to monitor ETCO2 in conjunction with a nasal cannula configured to deliver oxygen to a patient.

Figure 2C:
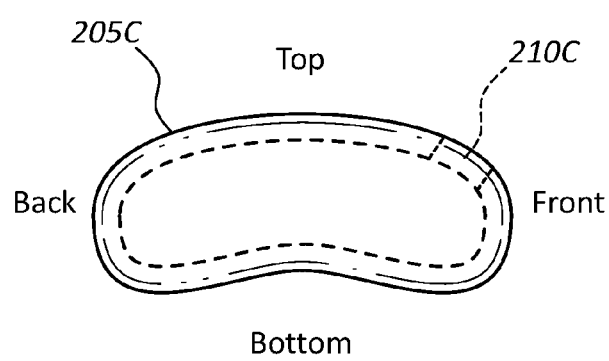

As illustrated, FIG. 2C depicts a cross-sectional view of a chamber 205C. In some embodiments, FIG. 2C depicts one example of a chamber for collecting respiratory gases. In one embodiment, chamber 205C may depict an example of a cross-section of chamber 105C depicted in FIG. 1C. As shown in FIG. 2C, chamber 205C includes at least one breathing port 210C. As depicted, chamber 205C is configured in the shape of a kidney or reniform prism. As with the breathing ports 110C of FIG. 1C, the at least one breathing port 210C may be configured to capture respiratory gases and collect them into chamber 205C. The at least one breathing port 210C may be located on a portion of the surface of the reniform chamber 205C. As illustrated, the portion of the surface of chamber 205C upon which the at least one breathing port 210C may be located may be referred to as a front surface. The portion of the surface of chamber 205C opposite that of the portion of the surface containing the at least one breathing port 210C, as illustrated, may be referred to a back surface. If the cross-sectional view of chamber 205C were divided into 360 degrees, with the portion of surface of chamber 205C containing the at least one breathing port 210C near 0 degrees, then the back surface would be situated near 180 degrees. Furthermore, a portion of the surface of chamber 205C at 90 degrees may be referred to as a top surface of chamber 205C, and a portion of the surface of chamber 205C at 270 degrees may be referred to as a bottom surface of chamber 205C. Thus, relative to the chamber 205C resting on a flat surface such as a desktop or medical tray, the surface of chamber 205C resting on the flat surface of the desktop or tray may be referred to as the bottom surface of chamber 205C and the surface of the chamber 205C opposite the bottom surface may be referred to as the top surface. In some embodiments, chamber 205C may collect expired CO2. Thus, in some cases, chamber 205C may be used to monitor ETCO2 in conjunction with a nasal cannula configured to deliver oxygen to a patient.

Figure 2D:
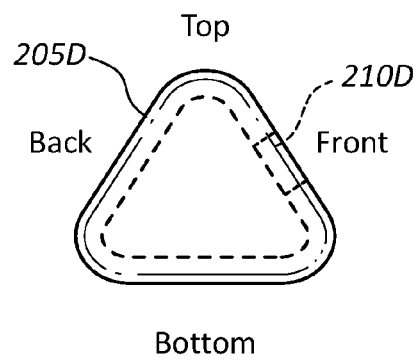
Figure 3:
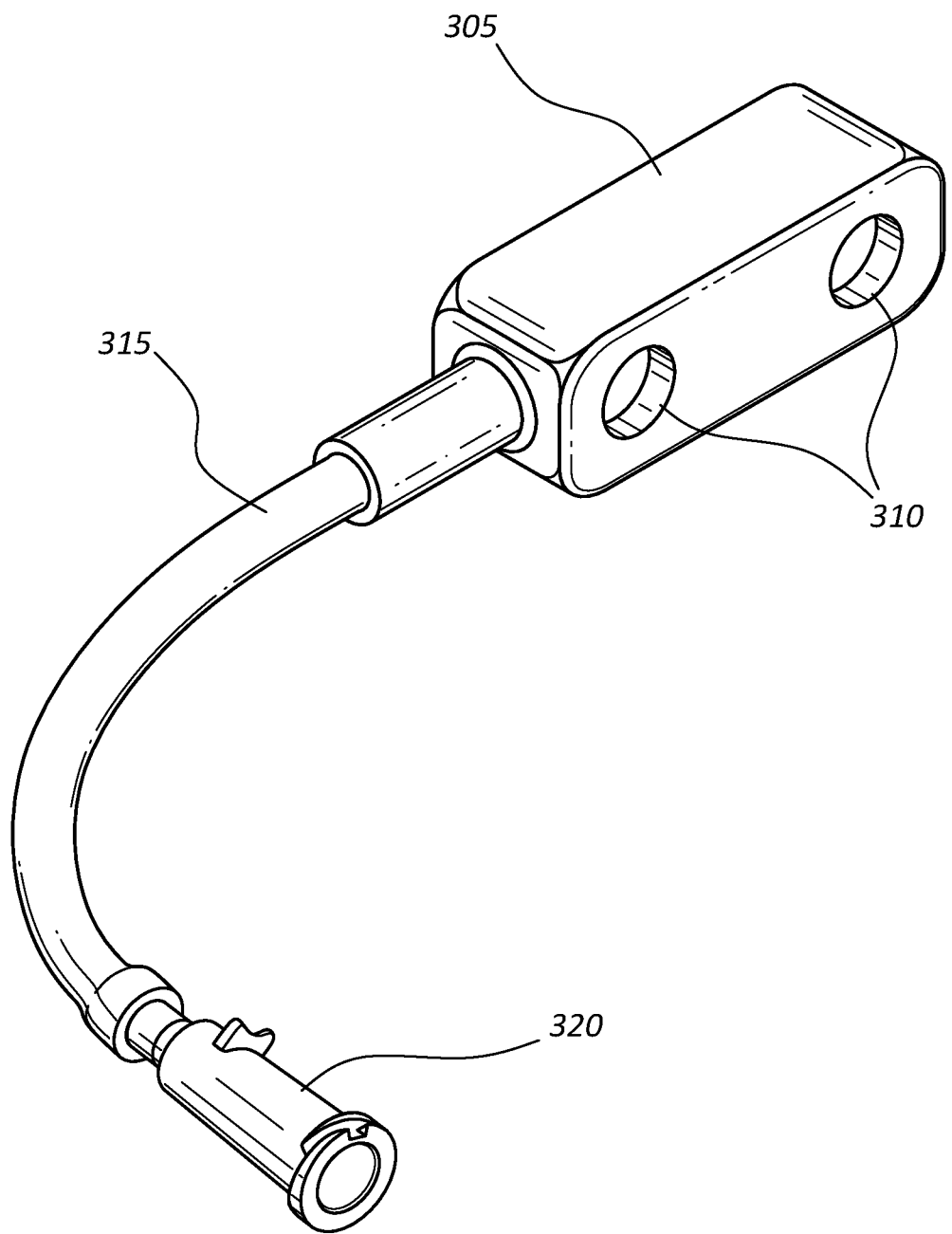
FIG. 3 is a diagram illustrating one example of a perspective of a chamber with a connection stem.

As illustrated, FIG. 2D depicts a cross-sectional view of a chamber 205D. In some embodiments, FIG. 2D depicts one example of a chamber for collecting respiratory gases. In one embodiment, chamber 205D may depict an example of a cross-section of chamber 105D depicted in FIG. 1D. As shown in FIG. 2D, chamber 205D includes at least one breathing port 210D. As depicted, chamber 205D is configured in the shape of a deltoid or triangular prism. As with the breathing ports 110D of FIG. 1D, the at least one breathing port 210D may be configured to capture respiratory gases and collect them into chamber 205D. The at least one breathing port 210D may be located on a surface of the triangular chamber 205D. As illustrated, the triangular chamber 205D may include three surfaces and three vertices. Accordingly, a first of the three surfaces may be referred to as a front surface. As illustrated, the front surface may include the at least one breathing port 210D. A second of the three surfaces may be referred to as a back surface of chamber 205D, and a third of the three surfaces may be referred to as a bottom surface. A vertex situated between the front and back surfaces may be referred to as a top. Thus, relative to the chamber 205D resting on a flat surface such as a desktop or medical tray, the surface of chamber 205D resting on the flat surface of the desktop or tray may be referred to as the bottom surface of chamber 205D and the vertex of the chamber 205D opposite the bottom surface may be referred to as the top of chamber 205D. In some embodiments, chamber 205D may collect expired $CO_2$. Thus, in some cases, chamber 205D may be used to monitor ETCO2 in conjunction with a nasal cannula configured to deliver oxygen to a patient Referring now to FIG. 3, a chamber 305 is illustrated with two breathing ports 310. The breathing ports 310 may be located on the front surface of chamber 305. Although depicted with two breathing chambers 310, in some embodiments chamber 305 may include less or more than two breathing ports. Chamber 305 may be one example of any one of the chambers illustrated in FIGS. 1A-1D and/or 2A-2D (e.g., chambers 105A-D and/or 205A-D). As illustrated, chamber 305 may include a stem 315. Although depicted with a stem on one side surface of chamber 305, stem 315 of chamber 305 may be located on another side surface of chamber 305. The length of stem 315 as depicted may be within 1-2× the width of chamber 305. The width of chamber 305 may be measured as the longest distance across the front surface of chamber 305 as depicted. In one embodiment, the width of chamber 305 from the proximal side surface to which stem 315 attaches to chamber 305 to the opposite, distal side surface of chamber 305 may be at least 0.5 inches (1.27 cm). For instance, chamber 305 may be at least 0.5 inches wide and include one breathing port. In some embodiments, chamber 305 may be less than 0.5 inches in width. For example, chamber 305 may be configured with one breathing port in order to capture $CO_2$ expired from a single nostril. Thus, a first chamber may be positioned to capture $CO_2$ expired from the right nostril and a second chamber may be positioned to capture $CO_2$ expired from the left nostril. Additionally, or alternatively, a chamber may be positioned to capture $CO_2$ expired orally from the mouth. In some cases, chamber 305 may include a tube that extends from a surface of chamber 305 that is configured to capture orally expired $CO_2$ in addition to $CO_2$ expired from the nose.

Although the length of stem 315 is depicted as being within 1-2× the width of chamber 305, the length of stem 315 may be less or more than the length depicted. As depicted, stem 315 may include a connector 320. Connector 320 may include a standard type of connector used to monitor ETCO2. In some cases, connector 320 may include a proprietary connector to connect the chamber 305 to a $CO_2$ monitoring device configured to sample the $CO_2$ collected in the chamber 305 and generate a graph indicating the rate of expired $CO_2$ over time.

Figure 4:
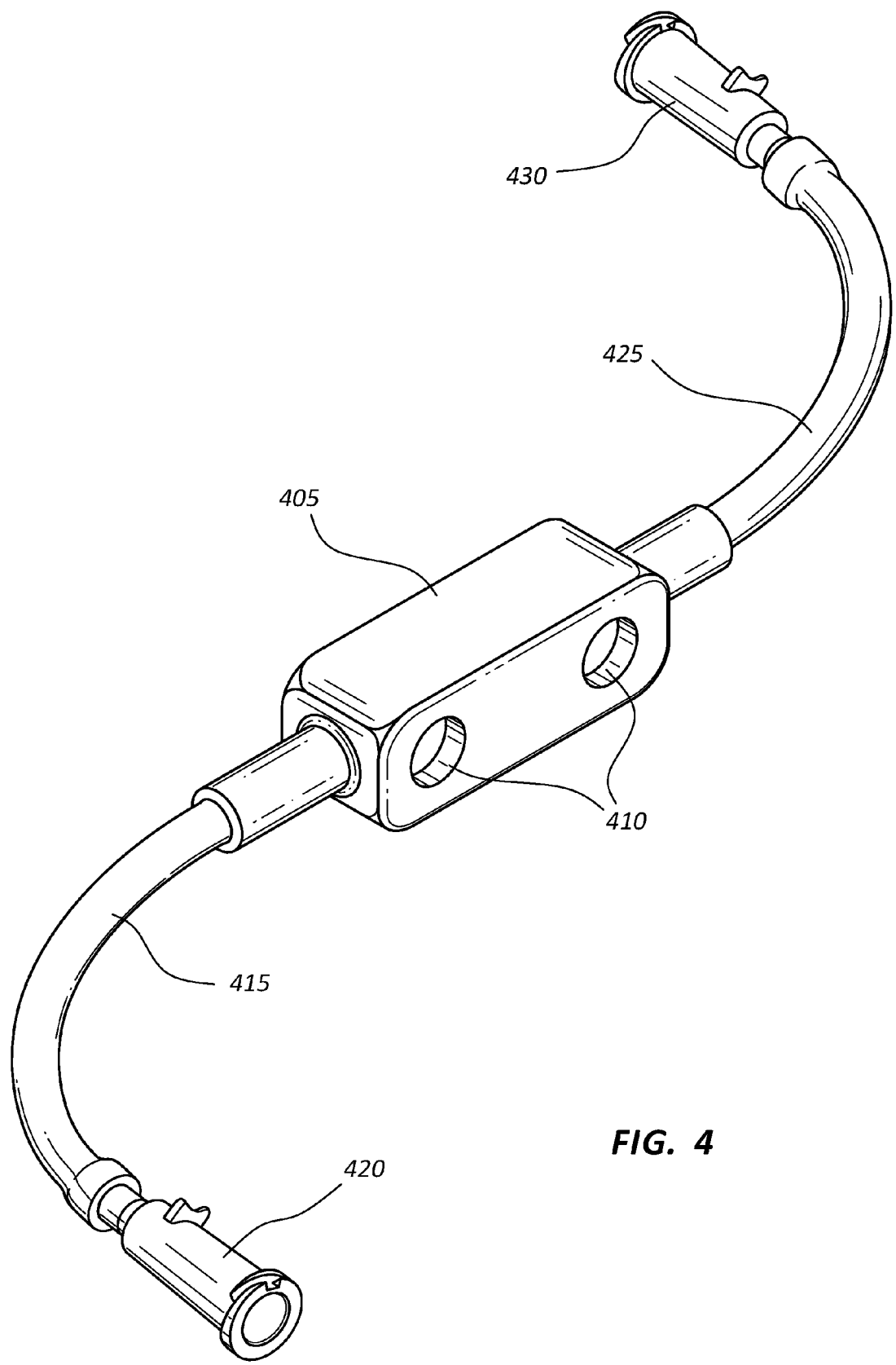
FIG. 4 is a diagram illustrating one example of a perspective of a chamber with two connection stems.

Referring now to FIG. 4, a chamber 405 is illustrated with two breathing ports 410. The breathing ports 410 may be located on the front surface of chamber 405. Although depicted with two breathing chambers 410, in some embodiments chamber 405 may include less or more than two breathing ports. Chamber 405 may be one example of any one of the chambers illustrated in FIGS. 1A-1D, 2A-2D, and/or FIG. 3 (e.g., chambers 105A-D, 205A-D, and/or 305). As illustrated, chamber 405 may include a first stem 415 and a second stem 425. The length of stems 415 and 425 as depicted may be within 1-2× the width of chamber 405. The width of chamber 405 may be measured as the longest distance across the front surface of chamber 405 as depicted. In one embodiment, the width of chamber 405 from the proximal side surface to which stem 415 attaches to chamber 405 to the opposite, distal side surface to which stem 425 attaches to chamber 405 may be at least 0.5 inches (1.27 cm). For instance, chamber 405 may be at least 0.5 inches wide and include one breathing port. Although the length of stems 415 and 425 is depicted as being within 1-2× the width of chamber 405, the length of stem 415 and/or 425 may be less or more than the length depicted. As depicted, stem 415 may include a connector 420. Similarly, stem 425 may include a connector 430. Connector 420 and/or 430 may include a standard type of connector used to monitor ETCO2. In some cases, connector 420 and/or 430 may include a proprietary connector to connect the chamber 405 to a $CO_2$ monitoring device configured to sample the $CO_2$ collected in the chamber 405 and generate a graph indicating the rate of expired $CO_2$ over time. In some embodiments, connector 420 may be of a first type of connector and connector 430 may be of a second type of connector, where the first type of connector is different from the second type of connector.

Figure 5A:
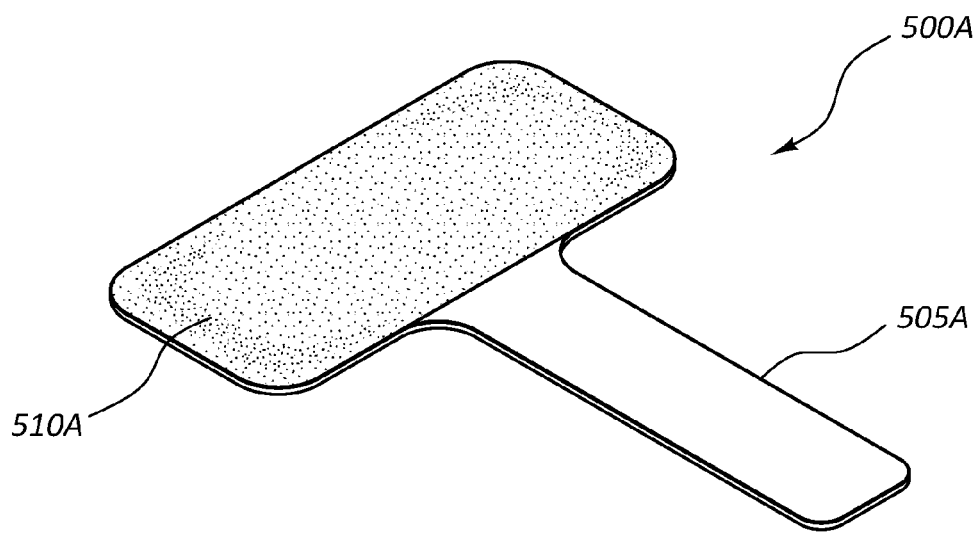
FIG. 5A illustrates a perspective view of a top surface of an adhesive pad with a strip extending from the adhesive pad.
Figure 5B:
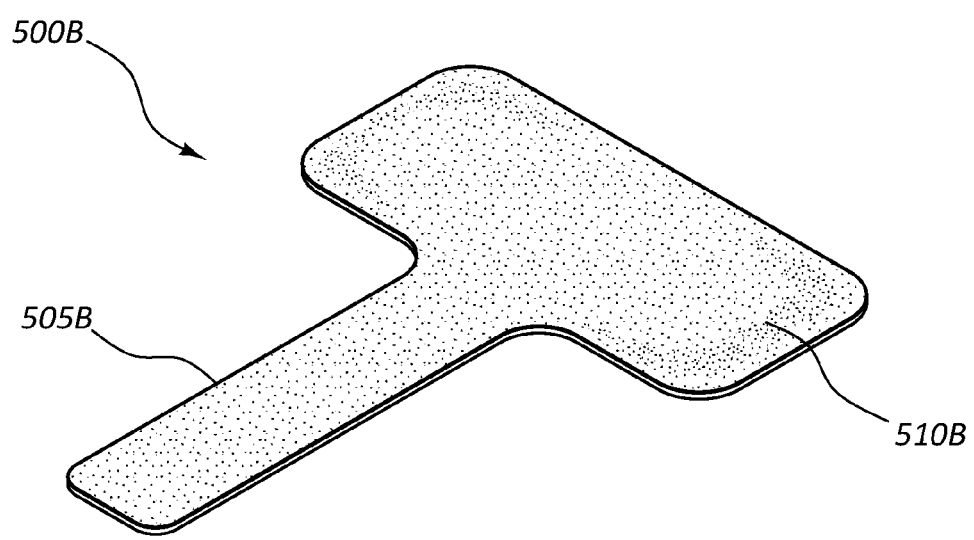
FIG. 5B illustrates a perspective view of a bottom surface of the adhesive pad of FIG. 5A with the strip extending from the adhesive pad.

Referring now to FIGS. 5A and 5B, FIG. 5A depicts an adhesive pad 500A. In one embodiment, the adhesive pad 500A depicted in FIG. 5A may be referred to as a top side of adhesive pad 500A. The adhesive pad 500A may include a substrate 505A and an adhesive 510A. In one embodiment, substrate 505A may be made from any combination of plastics, poly vinyl chloride (PVC), latex, silicone, natural polymers, synthetic polymers, and the like. Adhesive 510A may include any combination of natural adhesives, synthetic adhesives, drying adhesives, pressure-sensitive adhesives (e.g., acrylate based polymers), contact adhesives, hot adhesives, reactive adhesives, non-reactive adhesives, multi-part adhesives (e.g., epoxies, polymer resins, solvent-based, solvent-less), one-part adhesives (e.g., light curing adhesives, heat curing adhesives, moisture curing adhesives), and the like. As depicted, substrate 505A may include a pad portion (e.g., portion of substrate 505A covered with adhesive 510A) and a strip or band portion that extends from the pad portion. Adhesive pad 500A may be configured in a T-shape or hammer shape (e.g., the pad making up the head of the hammer shape and the strip making up the handle of the hammer shape). In some embodiments, adhesive pad 500A may be configured with other shapes. As seen in FIG. 5A, substrate 505A may encompass the entire T-shape of the adhesive pad 500A. As depicted, adhesive 510A may cover at least a portion of substrate 505A. Thus, taking the adhesive pad 500A as being in a hammer shape, the substrate 505A may make up both the handle as well as the head of the hammer-shaped adhesive pad 500A. On the other hand, adhesive 510A may be applied to and cover only a portion of substrate 505A. For example, as depicted, adhesive 510A may be applied to and cover substrate 505A on the head of the hammer shaped adhesive pad 500A. In some embodiments, adhesive 510A may cover less or more of substrate 505A than as depicted. For example, in some cases, adhesive 510A may cover the entire top surface of substrate 505A.

Referring now to FIG. 5B, FIG. 5B depicts an adhesive pad 500B. In one embodiment, the adhesive pad 500B depicted in FIG. 5B may be referred to as a bottom side of adhesive pad 500B. Adhesive pad 500B may be one example of adhesive pad 500A. The adhesive pad 500B may include a substrate 505B and an adhesive 510B. Substrate 505B may be one example of substrate 505A. For example, FIG. 5A may depict a top side and FIG. 5B depict a bottom side of the same substrate. Thus, substrate 505B and adhesive 510B may each be made from the same materials as substrate 505A and adhesive 510A, respectively. As depicted, adhesive 510B may cover at least a portion of substrate 505B. Thus, taking the adhesive pad 500B as being in a hammer shape, the substrate 505B may make up both the handle as well as the head of the hammer shaped adhesive pad 500B. In some embodiments, adhesive 510B may be applied to and cover the entire bottom surface of substrate 505B. For example, as depicted, adhesive 510B may be applied to and cover substrate 505B on both the head of the hammer shaped adhesive pad 500B as well as the handle of the hammer shaped adhesive pad 500B. In some embodiments, adhesive 510A may cover less of substrate 505A than as depicted. For example, in some cases, adhesive 510A may cover a portion of the head of the hammer shape and/or a portion of the handle of the hammer shape of substrate 505B.

Figure 6:
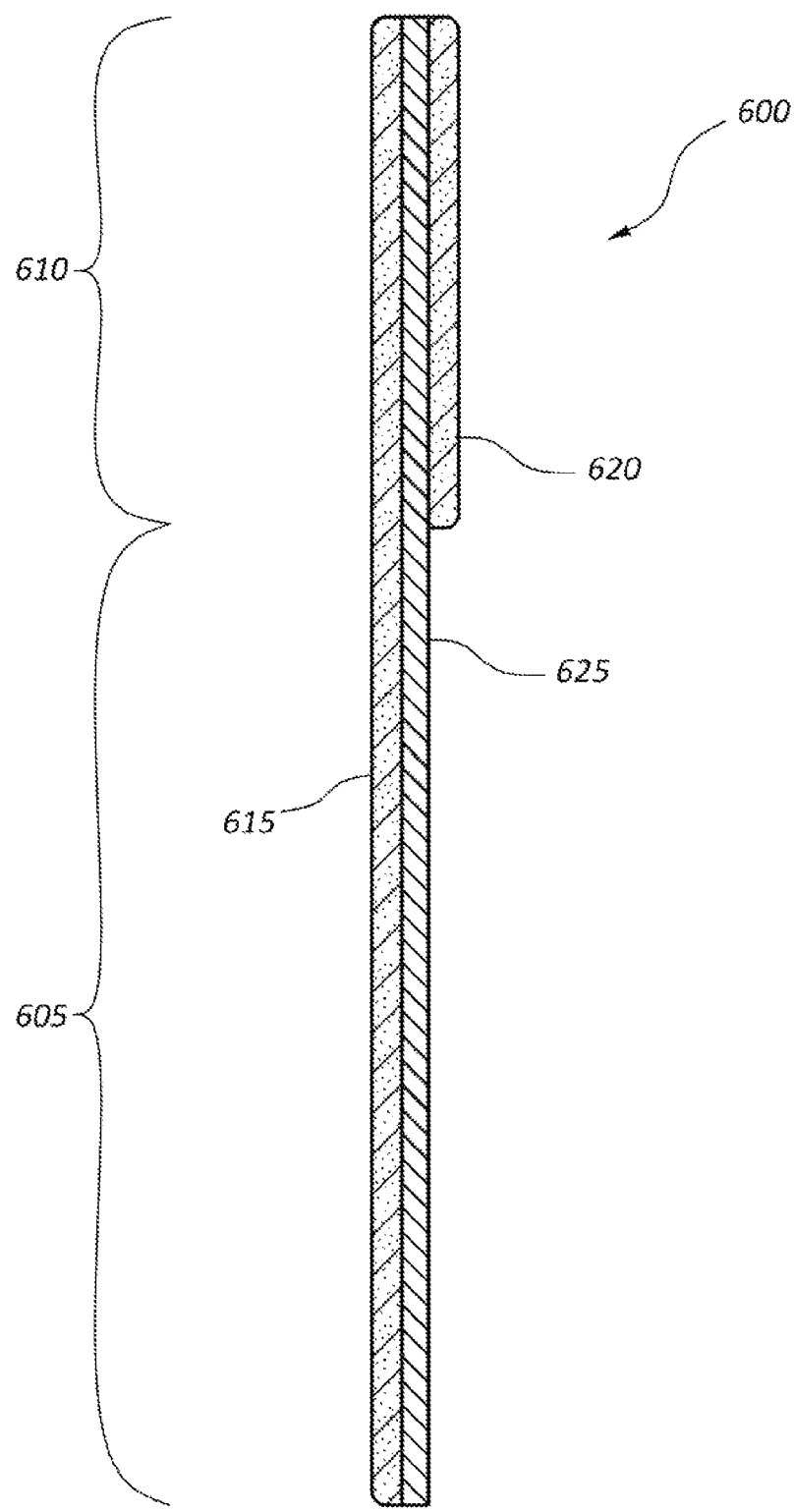
FIG. 6 illustrates a side-view of the adhesive pad of FIGS. 5A and 5B with the strip extending from the adhesive pad including a substrate layer and layers of adhesive on the top and bottom surface of the substrate layer.

Referring now to FIG. 6, FIG. 6 depicts a side view of adhesive pad 600. Adhesive pad 600 may be one example of adhesive pads 500A and/or 500B. Although not decipherable from the depiction illustrated in FIG. 6, the adhesive pad 600 may be in the T shape or hammer shape of the adhesive pads depicted in FIG. 5. For example, pad portion 610 of substrate 625 may denote the head of a hammer-shaped adhesive pad 600 and strip portion 605 of substrate 625 may denote a handle of a hammer-shaped adhesive pad 600, the strip portion 605 extending from the pad portion 610. Accordingly, adhesive pad 600 may include a substrate 625, bottom adhesive 615, and top adhesive 620. Substrate 625 may be one example of substrate 505A of FIG. 5A and/or substrate 505B of FIG. 5B. Bottom adhesive 615 may be one example of adhesive 510B of FIG. 5B. Top adhesive 620 may be one example of adhesive 510A of FIG. 5A. As depicted, bottom adhesive 615 may be applied to a bottom surface of substrate 625. Bottom adhesive 615, in some embodiments, may be applied to an entire bottom surface of substrate 625 (e.g., on bottom side of pad portion 610 of substrate 625 and bottom side of strip portion 605 of substrate 625). Top adhesive 620 may be applied to a top surface of substrate 625. In some embodiments, top adhesive 620 may be applied to just a portion of a top surface of substrate 625. For example, top adhesive 620 may be applied to a top side of pad portion 610 of substrate 625, whereas a top side of strip portion 605 of substrate 625 may be void of adhesive 620.

Figure 7:
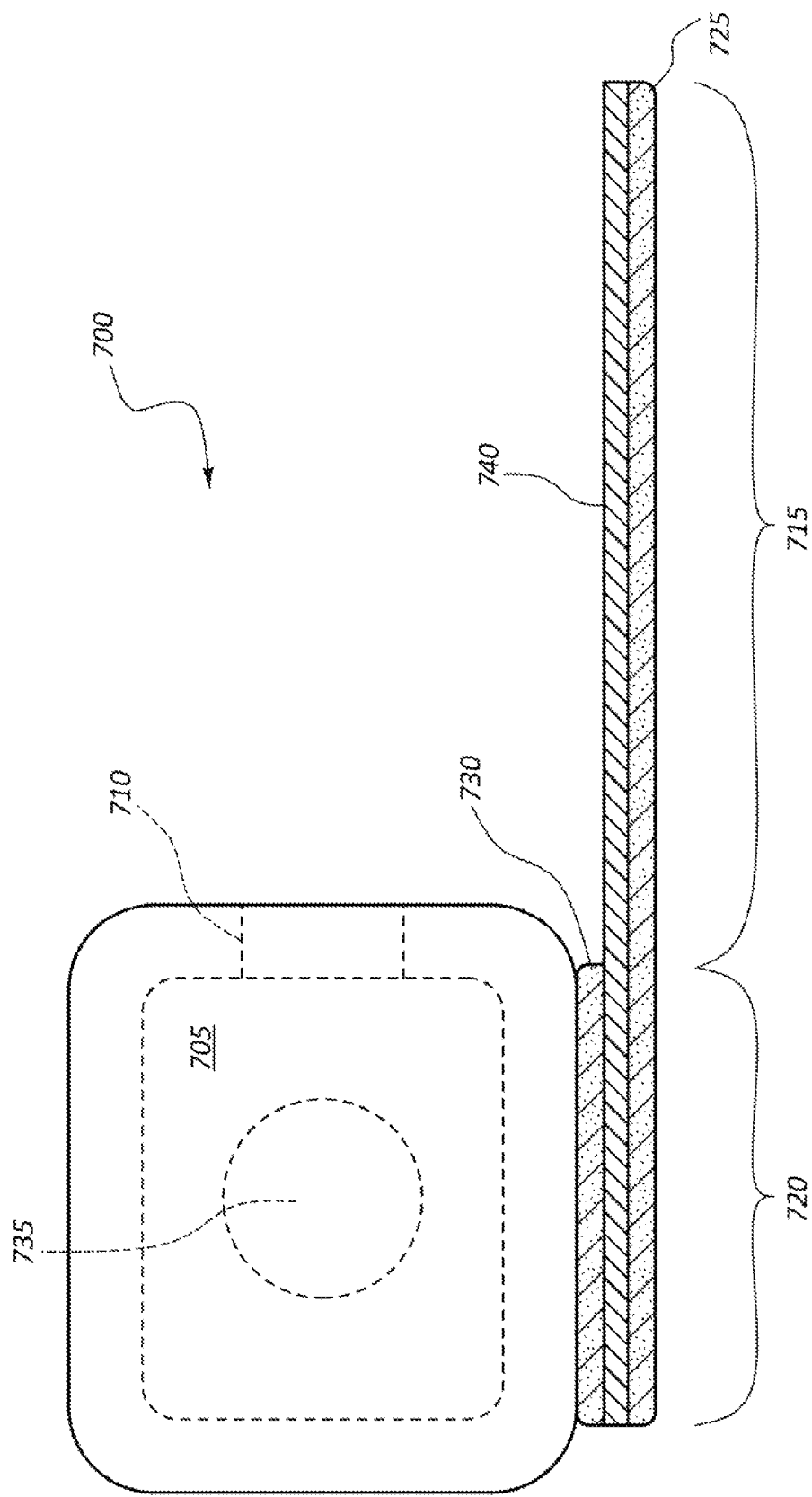
FIG. 7 illustrates a side-view of a chamber attached to a top surface of the adhesive pad of FIGS. 5A, 5B, and/or 6.

Referring now to FIG. 7, FIG. 7 depicts a side view of an attachable nasal cannula 700. The attachable nasal cannula 700 may include a chamber 705 and an adhesive pad that includes a pad portion 720 and a strip portion 715. The substrate 740 of the adhesive pad may extend from the pad portion 720 to the strip portion 715. In one embodiment, substrate 740 may be in a hammer shape similar to that of the adhesive pads depicted in FIGS. 5A and 5B. Thus, chamber 705 may be one example of any one of the chambers illustrated in FIGS. 1A-1D, 2A-2D, FIG. 3, and/or FIG. 4 (e.g., chambers 105A-D, 205A-D, 305, and/or 405). Substrate 740 may be one example of substrate 505A, 505B, and/or 625 of FIGS. 5 and 6. Accordingly, the pad portion 720 may be one example the pad portion 610 depicted in FIG. 6 (e.g., the head portion of a hammer-shaped adhesive pad), and strip portion 715 may be one example of strip portion 605 depicted in FIG. 6 (e.g., the handle portion of a hammer-shaped adhesive pad).

As depicted, chamber 705 may include at least one breathing port 710 located on a front surface of chamber 705. Chamber 705 may include at least one stem 735 located on a side surface of chamber 705. As illustrated, a top surface of substrate 740 may include a top adhesive 730. A bottom surface of substrate 740 may include a bottom adhesive 725. The top adhesive 730, in some embodiments, may cover and be applied to at least a portion of the top surface of substrate 740. For example, top adhesive 730 may be applied to the top of pad portion 720 of substrate 740. Similarly, bottom adhesive 725 may be applied to at least a portion of the bottom surface of substrate 740. For example, bottom adhesive 725 may be applied to the bottom of pad portion 720 and bottom of strip portion 715 of substrate 740. Accordingly, as illustrated top adhesive 730 may attach to a bottom surface of chamber 705, affixing substrate 740 to chamber 705, enabling chamber 705 to attach to a nasal cannula via bottom adhesive 725.

Figure 8:
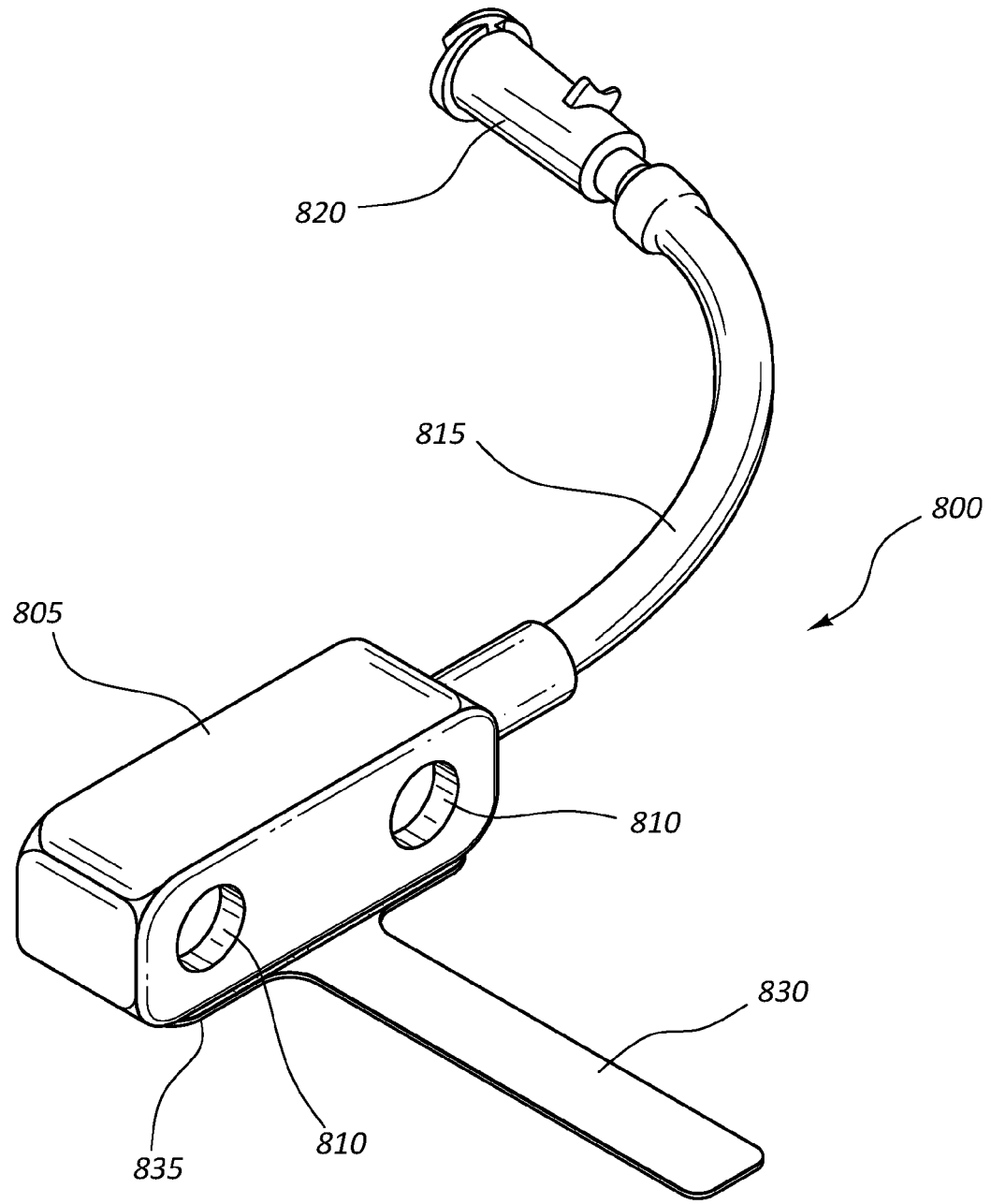
FIG. 8 illustrates a perspective view of the chamber and adhesive pad of FIG. 7.

Referring now to FIG. 8, FIG. 8 depicts one example of a perspective view of an attachable nasal cannula 800. Attachable nasal cannula 800 may be one example of attachable nasal cannula 700 of FIG. 7. As depicted, attachable nasal cannula 800 includes a chamber 805, breathing ports 810, stem 815, and connector 820. Additionally, attachable nasal cannula 800 may include an adhesive pad 830. The adhesive pad 830 may include a pad portion 835. As illustrated, a strip portion may extend from the pad portion 835 of the adhesive pad 830. The breathing ports 810 may be located on a front surface of chamber 805. Stem 815 may be located on a side surface of chamber 805. The chamber 805 may attach to the pad portion 835 of the adhesive pad 830. For example, the pad portion 835 of the adhesive pad 830 may include an adhesive, joining the chamber 805 to the adhesive pad 830.

Figure 9:
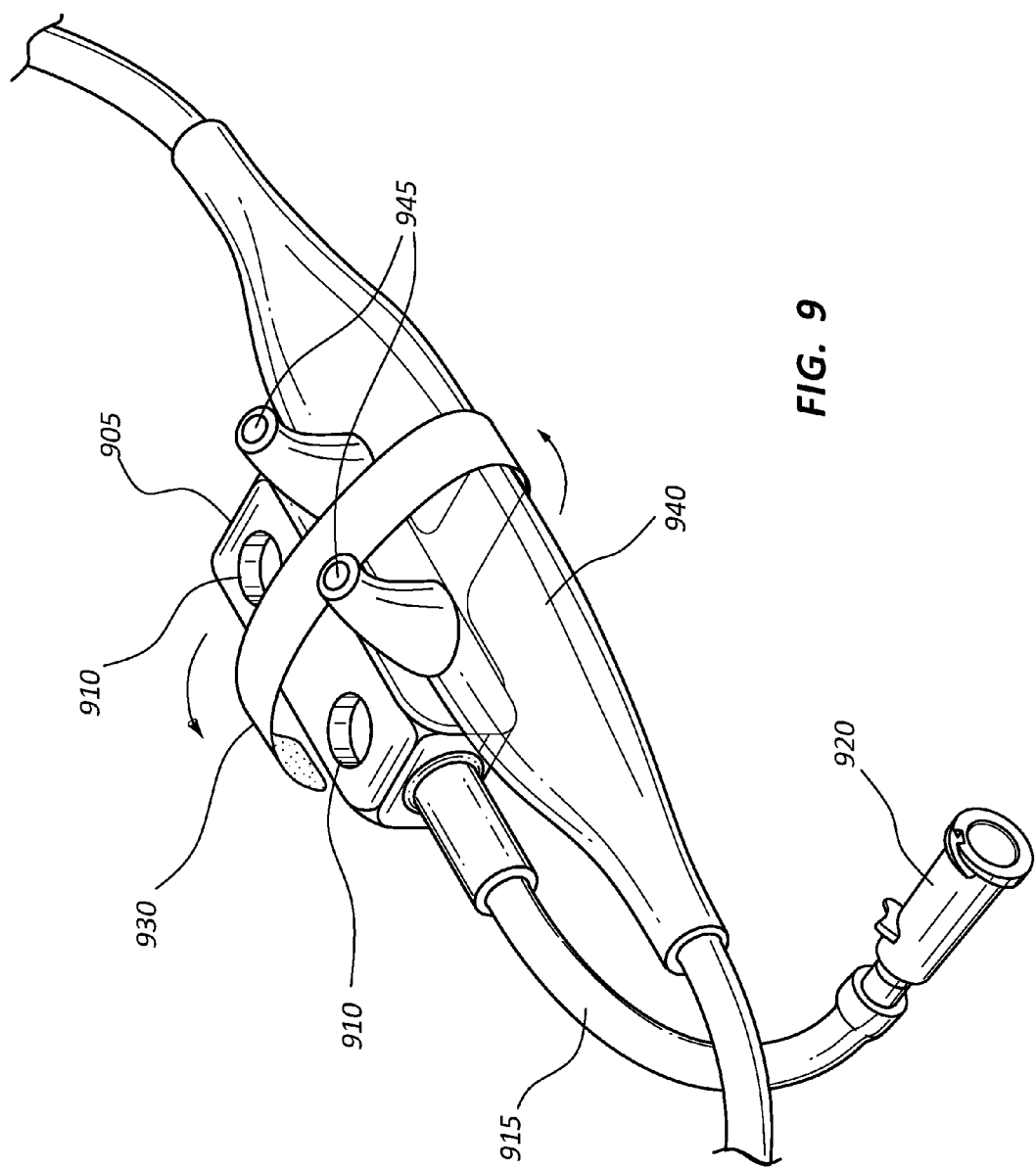
FIG. 9 illustrates a perspective view of a chamber and adhesive pad being attached to a conventional nasal cannula.

Referring now to FIG. 9, FIG. 9 depicts an attachable nasal cannula. The attachable nasal cannula is composed of chamber 905 and adhesive pad 930. Thus, chamber 905 attaches to a conventional nasal cannula 940 via adhesive pad 930. The conventional nasal cannula 940 includes breathing prongs 945. The chamber 905 and adhesive pad 930 of the attachable nasal cannula of FIG. 9 may be one example of the chamber 805 and adhesive pad 830 of FIG. 8 and/or the attachable nasal cannula 700 of FIG. 7. As depicted in FIG. 9, a pad portion of the adhesive pad 930 adhesively attaches to a bottom surface of chamber 905 and to a top surface of the conventional nasal cannula 940.

In some embodiments, a strip portion of the adhesive pad 930 may extend from a pad portion of the adhesive pad 930. As seen in FIGS. 7 and 8, with the adhesive pad attached to the chamber, the strip portion of the adhesive pad may extend out in front of the front surface of the chamber (i.e., the front surface being where the one or more breathing ports are located). As depicted in FIG. 9, with the strip portion of the adhesive pad 930 attached to chamber 905, instead of extending out in front of the front surface of chamber 905 the strip portion of the adhesive pad 930 may extend out behind the back surface of chamber 905. Accordingly, adhesive may be applied to the top and bottom surfaces of adhesive pad 930 to accommodate either configuration.

The attachable nasal cannula of FIG. 9 includes a chamber 905 and an adhesive pad 930. The chamber 905 includes breathing ports 910, stem 915, and connector 920. The adhesive pad 930 includes a bottom surface and a top surface. As depicted in FIG. 9, a pad portion of the top surface of adhesive pad 930 includes an adhesive attached to a bottom surface of chamber 905. A strip portion of the adhesive pad 930 extends from the pad portion of the adhesive pad 930. A bottom surface of the adhesive pad 930 may include an adhesive. The adhesive on the bottom surface of the adhesive pad (similar to bottom adhesive 725 of FIG. 7) may attach the adhesive pad 930 to a surface of the conventional nasal cannula 940. Additionally, as depicted, the strip portion of the adhesive pad 930 may be wrapped around the conventional nasal cannula 940. The adhesive on the bottom surface of the strip portion of the adhesive pad 930 may provide further attachment between the chamber 905 of the attachable nasal cannula and the conventional nasal cannula 940 by wrapping adhesive pad 930 around the conventional nasal cannula 940 and chamber 905, securing the two to each other via adhesive.

Figure 10:
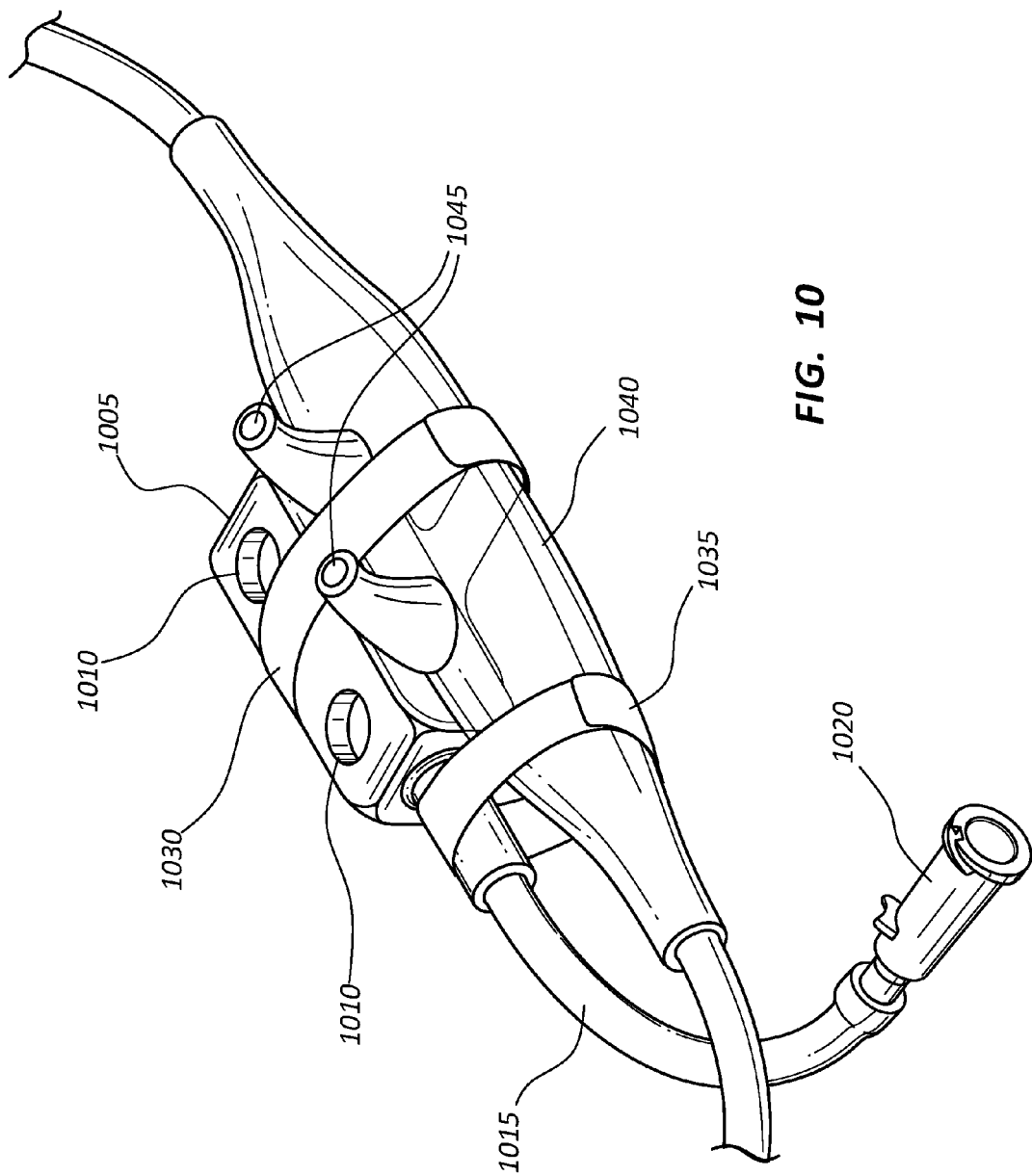
FIG. 10 illustrates a perspective view of a chamber and adhesive pad attached to a conventional nasal cannula via the adhesive pad and a flexible adhesive strip.

Referring now to FIG. 10, FIG. 10 depicts an attachable nasal cannula. The attachable nasal cannula is composed of chamber 1005, an adhesive pad 1030, and an adhesive stem strip 1035. Thus, as depicted, chamber 1005 attaches to a conventional nasal cannula 940 via adhesive pad 1030 and adhesive stem strip 1035. The conventional nasal cannula 1040 includes breathing prongs 1045. The chamber 1005 and adhesive pad 1030 of the attachable nasal cannula of FIG. 10 may be one example of the chamber 905 and adhesive pad 930 of FIG. 9, chamber 805 and adhesive pad 830 of FIG. 8, and/or the attachable nasal cannula 700 of FIG. 7. As depicted in FIG. 10, a pad portion of the adhesive pad 1030 adhesively attaches to a bottom surface of chamber 1005 and to a top surface of the conventional nasal cannula 1040. An adhesive stem strip 1035 wraps around the stem 1015 and a portion of the conventional nasal cannula 1040 (e.g., a stem of conventional nasal cannula 1040) to provide further attachment.

The chamber 1005 includes breathing ports 1010, stem 1015, and connector 1020. The adhesive pad 1030 includes a bottom surface and a top surface. As depicted in FIG. 10, a pad portion of the top surface of adhesive pad 1030 includes an adhesive attached to a bottom surface of chamber 1005. A strip portion of the adhesive pad 1030 extends from the pad portion of the adhesive pad 1030. A bottom surface of the adhesive pad 1030 may include an adhesive. The adhesive on the bottom surface of the adhesive pad 1030 (similar to bottom adhesive 725 of FIG. 7) may attach the adhesive pad 1030 to a surface of the conventional nasal cannula 1040.

In some embodiments, a strip portion of the adhesive pad 1030 may extend from a pad portion of the adhesive pad 1030 and wrap around the conventional nasal cannula and the chamber 1005, joining the two together. The adhesive stem strip 1035 may wrap around stem 1015, securing the adhesive stem strip 1035 to chamber 1005. The adhesive stem strip 1035 may then wrap around the stem 1015 of chamber 1005 and the conventional nasal cannula 1040, increasing the attachment between the chamber 1005 and conventional nasal cannula 1040. Accordingly, a medical professional may deliver oxygen to a patient via the conventional nasal cannula 1040 while simultaneously measuring CO2 via chamber 1005. Additionally, or alternatively, the medical professional may deliver oxygen to a patient via the chamber 1005 while simultaneously measuring CO2 via the conventional nasal cannula 1040.

Although adhesive pad 1030 is depicted with a pad portion adhesively attached to a bottom surface of chamber 1005, it is noted that the adhesive pad 1030 may attach to chamber 1005 using other techniques. For example, in some cases adhesive pad 1030 may include a strip that loops around chamber 1005, the strip looping around chamber 1005 and connecting to itself so that adhesive pad 1030. Thus, as an example, when a medical professional took chamber 1005 out of its packaging the adhesive pad 1030 would hand from chamber 1005. In this case, adhesive pad 1030 may not adhesively attach to chamber 1005, but instead adhesive pad 1030 may attach to chamber 1005 by looping entirely around chamber 1005 and connecting to itself adhesively forming a ring around chamber 1005. Thus, in some cases, adhesive pad 1030 may include only a strip portion without a pad portion (i.e., the handle only from a hammer-shaped adhesive pad, not the head shape). In any case, the adhesive pad 1030 may have a portion of adhesive on adhesive pad 1030 covered with a temporary covering. The medical professional may peel away this temporary covering to expose the adhesive. The medical professional may then loop adhesive pad 1030 around the conventional nasal cannula 1040 and chamber 1005, adhesively attaching the chamber 1005 to conventional nasal cannula 1040 via the looping adhesive pad 1030. Additionally, or alternatively, adhesive stem strip 1035 may include a temporary covering that may be removed to expose an adhesive. The medical professional may wrap the adhesive stem strip 1035 around stem 1015 and a stem of conventional nasal cannula 1040 to attach the chamber 1005 to conventional nasal cannula 1040 and/or provide additional attachment points. For example, the chamber 1005 may include two stems and two adhesive stem strips. For instance, chamber 1005 may include stem 1015 and a second stem such as the chamber 405 depicted in FIG. 4 with first stem 415 and second stem 425. Each of the two stems may include an adhesive stem strip. Thus, in addition to a medical professional attaching stem 1015 to conventional nasal cannula 1040 using adhesive stem strip 1035, the medical professional may attach the second stem of chamber 1005 to conventional nasal cannula 1040 using a second adhesive stem strip, providing additional points of attachment to further secure the pairing of chamber 1005 to conventional nasal cannula 1040.

Figure 11:
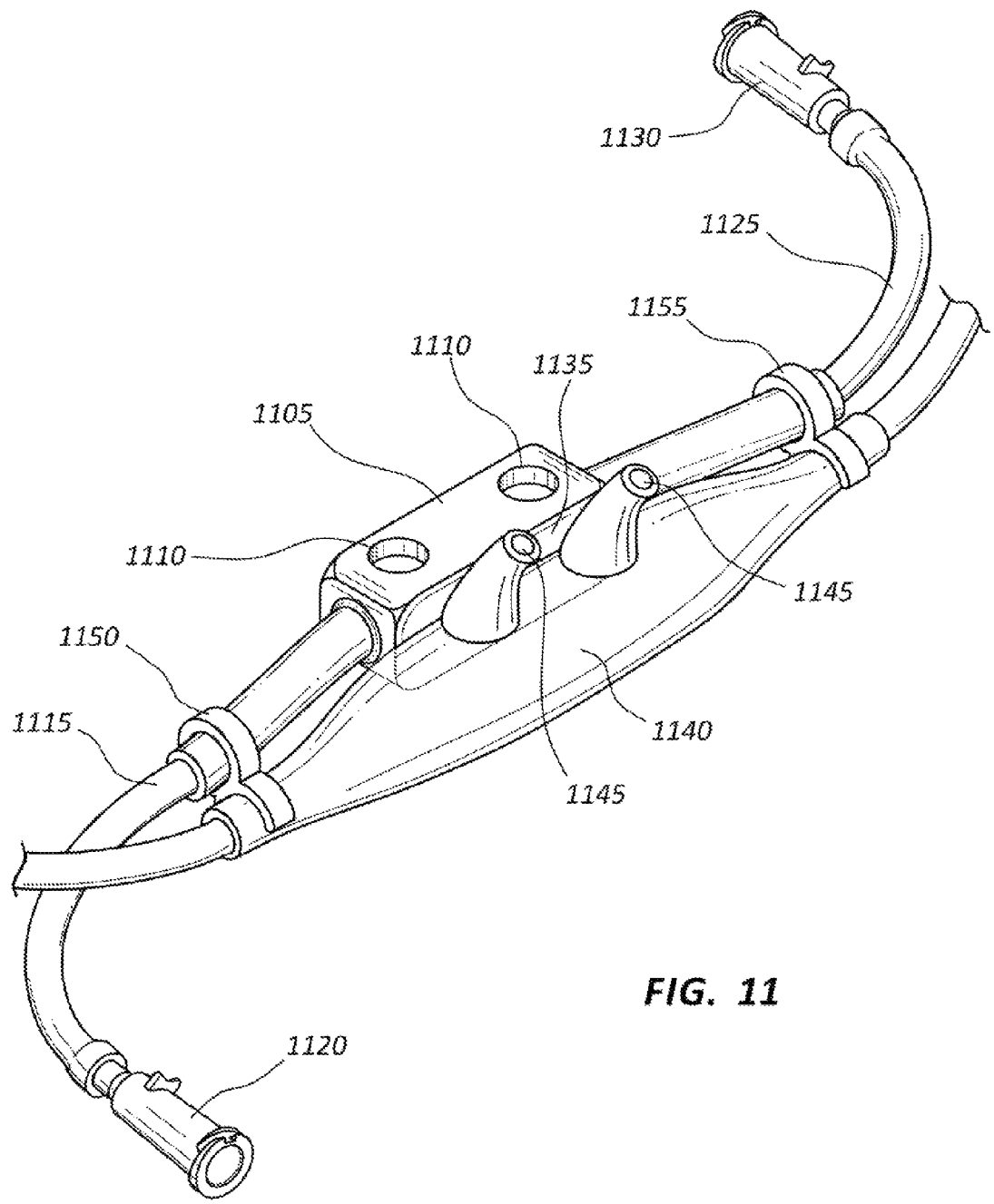
FIG. 11 illustrates a perspective view of a chamber and adhesive pad attached to a conventional nasal cannula via the adhesive pad and one or more clips.

It is noted that the attachable nasal cannula is configured to be attachable to any device. Although FIGS. 9 and 10 depict attaching an attachable nasal cannula to a conventional nasal cannula, it is understood that the attachable nasal cannula can be attached to any type of nasal cannula or any other type of device around which an adhesive pad and/or adhesive strip may be looped. Additionally, although FIGS. 5-10 depict an attachable nasal cannula with one or more adhesive devices, it is understood that other methods of attaching an attachable nasal cannula to a second nasal cannula are within the scope of the systems and methods described herein. For example, a non-adhesive strip may extend from a chamber of a nasal cannula. The non-adhesive strip may include one or more holes or perforations along the strip. The strip and/or chamber may include a hook by which the strap may be wrapped and set in place around another nasal cannula via the holes and hook. In some cases, the attachable nasal cannula may attach to another nasal cannula via a strap and buckle (e.g., snap lock buckle, side release buckle, center release buckle, curved side release buckle, etc.), and/or a strap and buttoning fastener. As depicted in FIG. 11, some embodiments of the attachable nasal cannula may include one or more clips.

Referring to FIG. 11, FIG. 11 depicts an attachable nasal cannula attached to a conventional nasal cannula 1140. The attachable nasal cannula includes a chamber 1105, adhesive pad 1135, and one or more clips 1150 and/or 1155. Chamber 1105 includes breathing ports 1110, first stem 1115, and second stem 1125. The first stem 1115 may include a first connector 1120. The second stem 1125 may include a second connector 1130. The conventional nasal cannula 1140 may include breathing prongs 1145. As depicted, first stem 1115 may include a first clip 1150. First clip 1150 may include a loop attachment to first stem 1115. As depicted, the loop attachment of clip 1150 to first stem 1115 may loop all the way around stem 1115, to some degree attaching clip 1150 to stem 1115 permanently. A semi-circular clip portion (e.g., not looping all the way around) may extend from this loop attachment portion first clip 1150, enabling first clip 1150 to attach to a stem portion of the conventional nasal cannula 1140. In some cases, first clip 1150 may include two semi-circular clip portions, one clip portion clipping to stem 1115 and a second clip portion clipping to a stem of the conventional nasal cannula 1140. Additionally, or alternatively, second stem 1125 may include a second clip 1155. Second clip 1155 may include a loop attachment to second stem 1125. A clipping portion may extend from this loop attachment of second clip 1155, enabling second clip 1155 to attach to a stem portion of the conventional nasal cannula 1140. In some cases, second clip 1155 may include two clip portions, one clip portion clipping to stem 1125 and a second clip portion clipping to a stem of the conventional nasal cannula 1140. In some cases, in addition to using clips, chamber 1105 may attach to the conventional nasal cannula 1140 via an adhesive pad 1135, where adhesive pad 1135 includes adhesive on a top and a bottom surface, the top surface of adhesive pad 1135 attaching to a bottom surface of chamber 1105, and the bottom surface of adhesive pad 1135 attaching to a top surface of conventional nasal cannula 1140, pairing chamber 1105 to conventional nasal cannula 1140.

Figure 12:
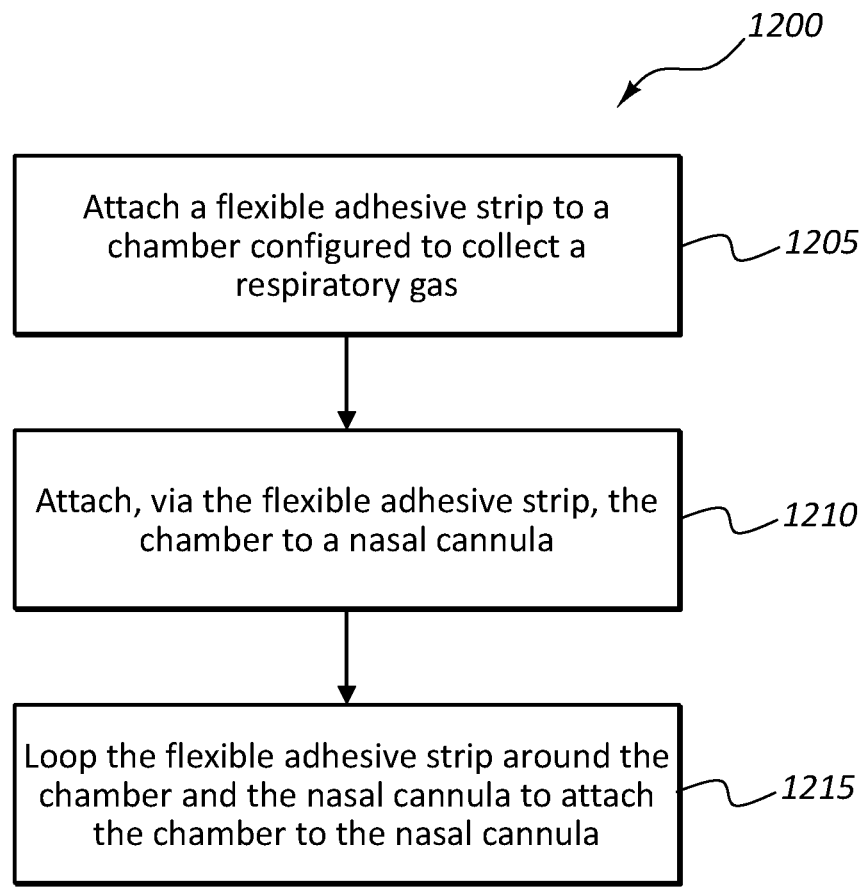
FIG. 12 is a flow diagram illustrating one embodiment of a method for an attachable nasal cannula.

Referring to FIG. 12, a flowchart of a method 1200 for assembling an attachable nasal cannula is depicted. For clarity, the method 1200 is described below with reference to the components of an attachable nasal cannula (e.g., chamber 805 and adhesive pad 830 of attachable nasal cannula 800 and/or equivalents thereof) of FIGS. 1A-D, 2A-D, 3, 4, 5A, 5B, 6, 7, 8, 9, 10 and/or 11.

At block 1205, a flexible adhesive strip may be attached to a chamber configured to collect a respiratory gas. At block 1210, the chamber may be attached to a nasal cannula via the flexible adhesive strip. At block 1215, the flexible adhesive strip may be looped around the chamber and the nasal cannula to attach the chamber to the nasal cannula. In some cases, the chamber may include a tubular stem extending from a surface of the chamber. The tubular stem may be configured as an outlet for respiratory gas collected in the chamber. In some cases, the tubular stem may include a flexible adhesive stem strip. The flexible adhesive stem strip may include a second substrate. At least a portion of the second substrate may be covered with adhesive. In one embodiment, the tubular stem may be attached to a tube of the nasal cannula by looping the flexible adhesive stem strip around the tubular stem and the tube of the nasal cannula. Therefore, the method 1200 may attach an attachable nasal cannula to a conventional nasal cannula to assemble a dual-purpose nasal cannula configured to deliver oxygen while monitoring CO2. It should be noted that the method 1200 is just one implementation and that the operations of the method 1200 may be rearranged or otherwise modified such that other implementations are possible.

The forgoing examples of using a rectangular prism chamber in FIGS. 3, 4, 7-11 are for illustrative purposes and not intended to be limiting. Any of the chambers described above in relation to FIGS. 1A-1D and/or 2A-2D may be used as a chamber of an attachable nasal cannula. As used in this specification and the appended claims, the term "tube" is used to refer to an elongated device with a passageway. The words "including" and "having," as well as their derivatives, as used in the specification, including the claims, have the same meaning as the word "comprising." The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A respiratory gas measurement system, the respiratory gas measurement system comprising:
    a chamber configured to collect a respiratory gas;
    an adhesive pad, the adhesive pad comprising a substrate, wherein the substrate comprises a first surface and a second surface and is in a shape of a club hammer comprising a head portion and a handle portion, and wherein the head portion of the first surface of the substrate is covered with adhesive and the handle portion of the first surface of the substrate is free of adhesive, and wherein both the head portion and the handle portion of the second surface of the substrate is covered with adhesive; and
    wherein the adhesive on the first surface of the substrate attaches the adhesive pad to a first surface of the chamber.

2. The respiratory gas measurement system of claim 1, further comprising:
    a nasal cannula, wherein the adhesive on the second surface of the substrate attaches the adhesive pad to a surface of the nasal cannula.

3. The respiratory gas measurement system of claim 1, wherein the handle portion of the adhesive pad is flexible and configured to loop around the chamber and a nasal cannula to attach the chamber to the nasal cannula.

4. The respiratory gas measurement system of claim 1, further comprising:
    at least one opening on a second surface of the chamber, the opening being configured as an inlet for the respiratory gas.

5. The respiratory gas measurement system of claim 1, further comprising:
    a tubular stem extending from a third surface of the chamber, the tubular stem configured as an outlet for the respiratory gas.

6. The respiratory gas measurement system of claim 5, wherein the tubular stem comprises a flexible adhesive stem strip, the flexible adhesive stem strip being configured to adhesively join the tubular stem to a tube of a nasal cannula.

7. The respiratory gas measurement system of claim 5, wherein the tubular stem comprises a connector, the connector being configured to enable measurement of the respiratory gas.

8. The respiratory gas measurement system of claim 5, wherein the tubular stem comprises a semi-circular clip, the semi-circular clip being configured to mechanically join the tubular stem to a tube of a nasal cannula.

9. An attachable nasal cannula, the attachable nasal cannula comprising:
    a chamber configured to collect a respiratory gas;
    an adhesive pad, the adhesive pad comprising a substrate, wherein the substrate comprises a first surface and a second surface and is in a shape of a club hammer comprising a head portion and a handle portion, and wherein the head portion of the first surface of the substrate is covered with adhesive and the handle portion of the first surface of the substrate is free of adhesive, and wherein both the head portion and the handle portion of the second surface of the substrate is covered with adhesive; and
    wherein the adhesive on the first surface of the substrate attaches the adhesive pad to a first surface of the chamber.

10. The attachable nasal cannula of claim 9, wherein the handle portion of the adhesive pad is flexible and configured to loop around the chamber and a nasal cannula to attach the chamber to the nasal cannula.

11. The attachable nasal cannula of claim 9, further comprising:
at least one opening on a second surface of the chamber, the opening being configured as an inlet for the respiratory gas.

12. The attachable nasal cannula of claim 9, further comprising:
a tubular stem extending from a third surface of the chamber, the tubular stem configured as an outlet for the respiratory gas.

13. The attachable nasal cannula of claim 12, further comprising:
a flexible adhesive stem strip attached to the tubular stem, the flexible adhesive stem strip being configured to adhesively join the tubular stem to a tube of a second nasal cannula.

14. The attachable nasal cannula of claim 12, further comprising:
a semi-circular clip attached to the tubular stem, the semi-circular clip being configured to mechanically join the tubular stem to a tube of a second nasal cannula.

15. A method for measuring respiratory gas, comprising:
attaching an adhesive pad to a chamber configured to collect a respiratory gas, the adhesive pad comprising a substrate, wherein the substrate comprises a first surface and a second surface and is in a shape of a club hammer comprising a head portion and a handle portion, and wherein the head portion of the first surface of the substrate is covered with adhesive and the handle portion of the first surface of the substrate is free of adhesive, and wherein both the head portion and the handle portion of the second surface of the substrate is covered with adhesive;
wherein the adhesive on the first surface of the substrate attaches the adhesive pad to a first surface of the chamber; and
attaching, via the second surface of the handle portion of the substrate, the chamber to a nasal cannula.

16. The method of claim 15, wherein the handle portion of the substrate is flexible, further comprising:
looping the handle portion of the substrate around the chamber and the nasal cannula to attach the chamber to the nasal cannula.

17. The method of claim 15, wherein the chamber comprises a tubular stem extending from a surface of the chamber, the tubular stem configured as an outlet for the respiratory gas collected in the chamber.

18. The method of claim 17, wherein the tubular stem comprises a flexible adhesive stem strip, the flexible adhesive stem strip comprising a second substrate, wherein at least a portion of the second substrate is covered with adhesive.

19. The method of claim 17, further comprising:
attaching the tubular stem to a tube of the nasal cannula by looping the flexible adhesive stem strip around the tubular stem and the tube of the nasal cannula.

* * * * *